US008219326B2

(12) United States Patent
Kurnik

(10) Patent No.: US 8,219,326 B2
(45) Date of Patent: *Jul. 10, 2012

(54) DETERMINATION OF MELTING TEMPERATURES OF DNA

(75) Inventor: Ronald T. Kurnik, Foster City, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 345 days.

This patent is subject to a terminal disclaimer.

(21) Appl. No.: 12/580,424

(22) Filed: Oct. 16, 2009

(65) Prior Publication Data

US 2010/0100363 A1    Apr. 22, 2010

Related U.S. Application Data

(63) Continuation-in-part of application No. 12/253,676, filed on Oct. 17, 2008, now Pat. No. 8,170,804.

(51) Int. Cl.
    *G01N 33/48*    (2006.01)

(52) U.S. Cl. ......................................................... 702/19
(58) Field of Classification Search ...................... 702/19
    See application file for complete search history.

*Primary Examiner* — Jerry Lin
(74) *Attorney, Agent, or Firm* — David J. Chang

(57) ABSTRACT

Numerical determinations of the first derivatives of a melt curve data set are made. A baseline is determined for the first derivative values and the baseline is subtracted from the first derivative values to produce modified first derivative values. A first maximum value of the modified first derivative values is determined and said first maximum value represents a melting temperature Tm of a DNA sample. A model function, such as a Gaussian Mixture Model (GMM) function, with parameters determined using a Levenberg-Marquardt (LM) regression process can also be used to find an approximation to the first derivative curve. The maximum values of the numerically determined first derivative values are used as initial conditions for parameters of the model function. The determined parameters provide one or more fractional melting temperature values, which can be returned, for example, displayed or otherwise used for further processing.

19 Claims, 12 Drawing Sheets

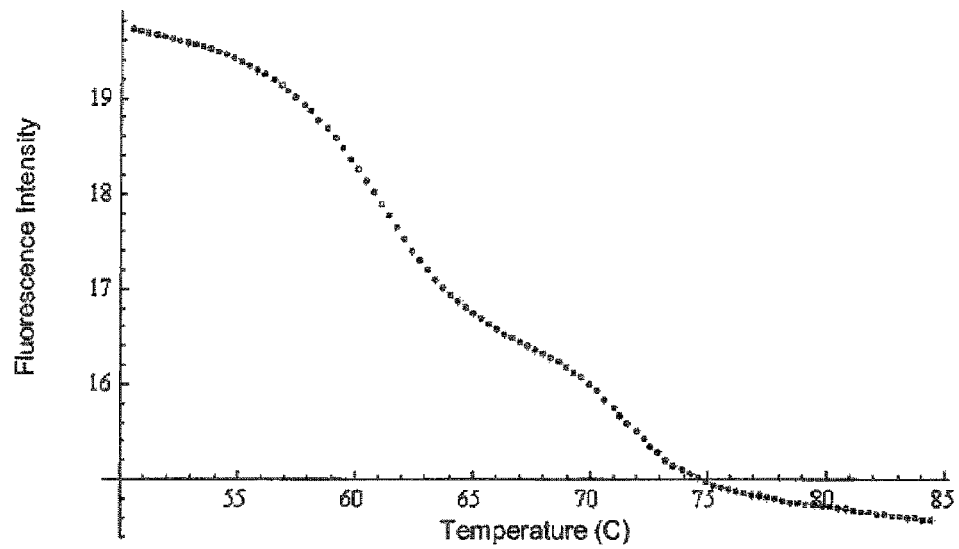
Figure 1: Fluorescence Intensity vs. Temperature
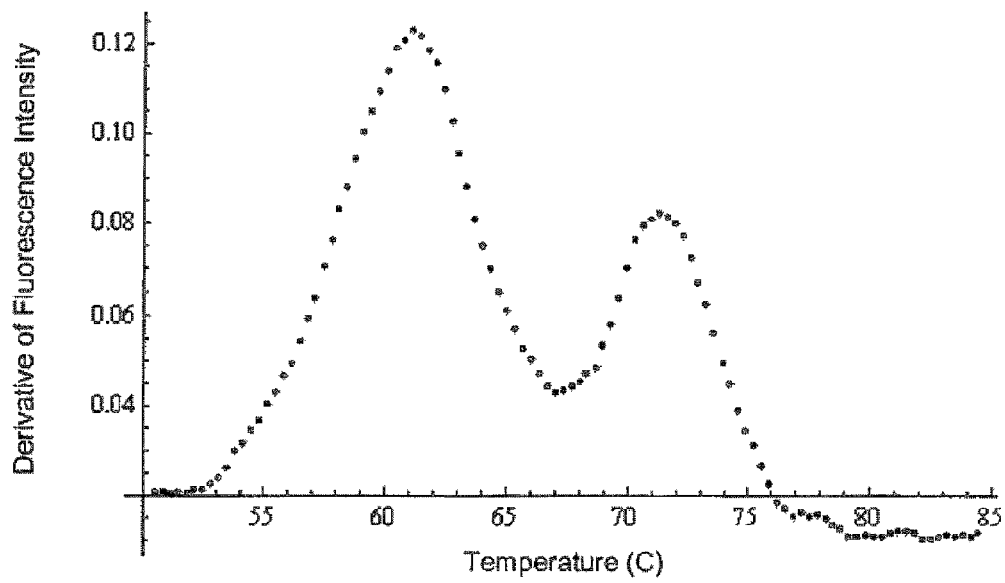
Figure 2: First Derivative of Fluorescence Intensity vs. Temperature

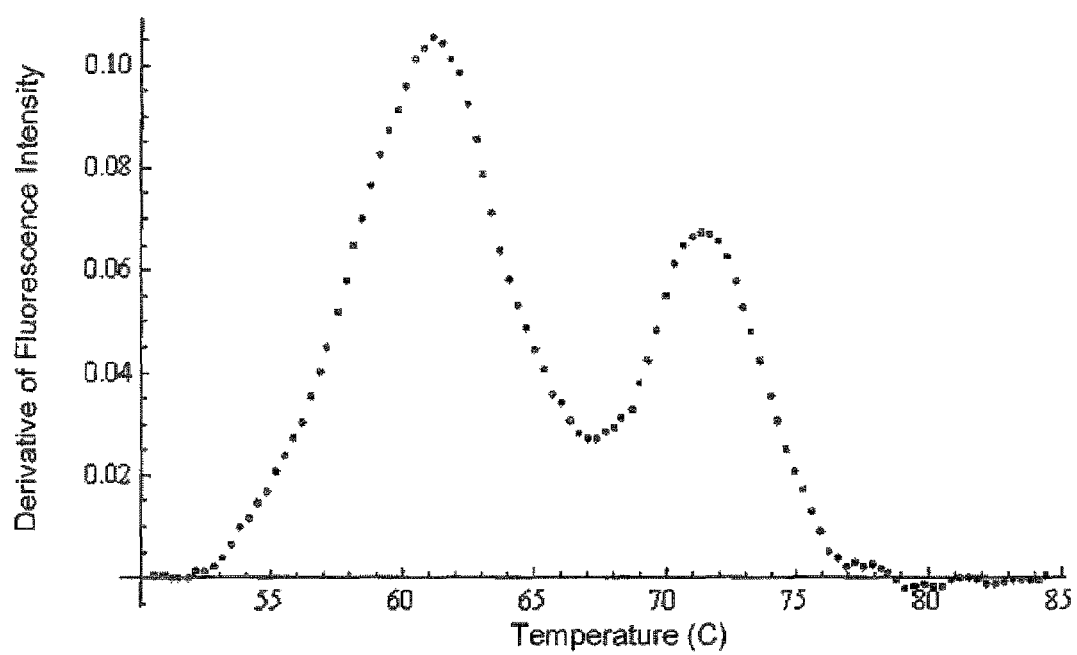
Figure 3: Baseline Subtracted First Derivative of Fluorescence Intensity vs. Temperature

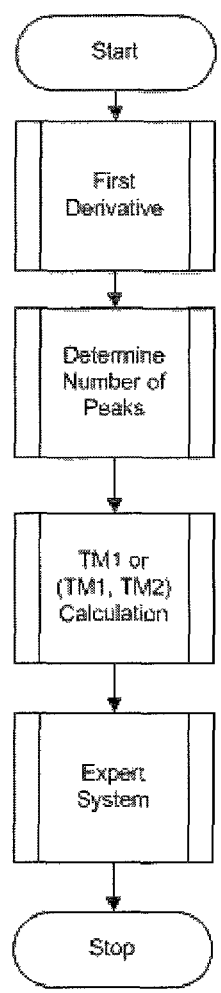
Figure 4: Major Processing Steps of the Equation-Less Melting Algorithm

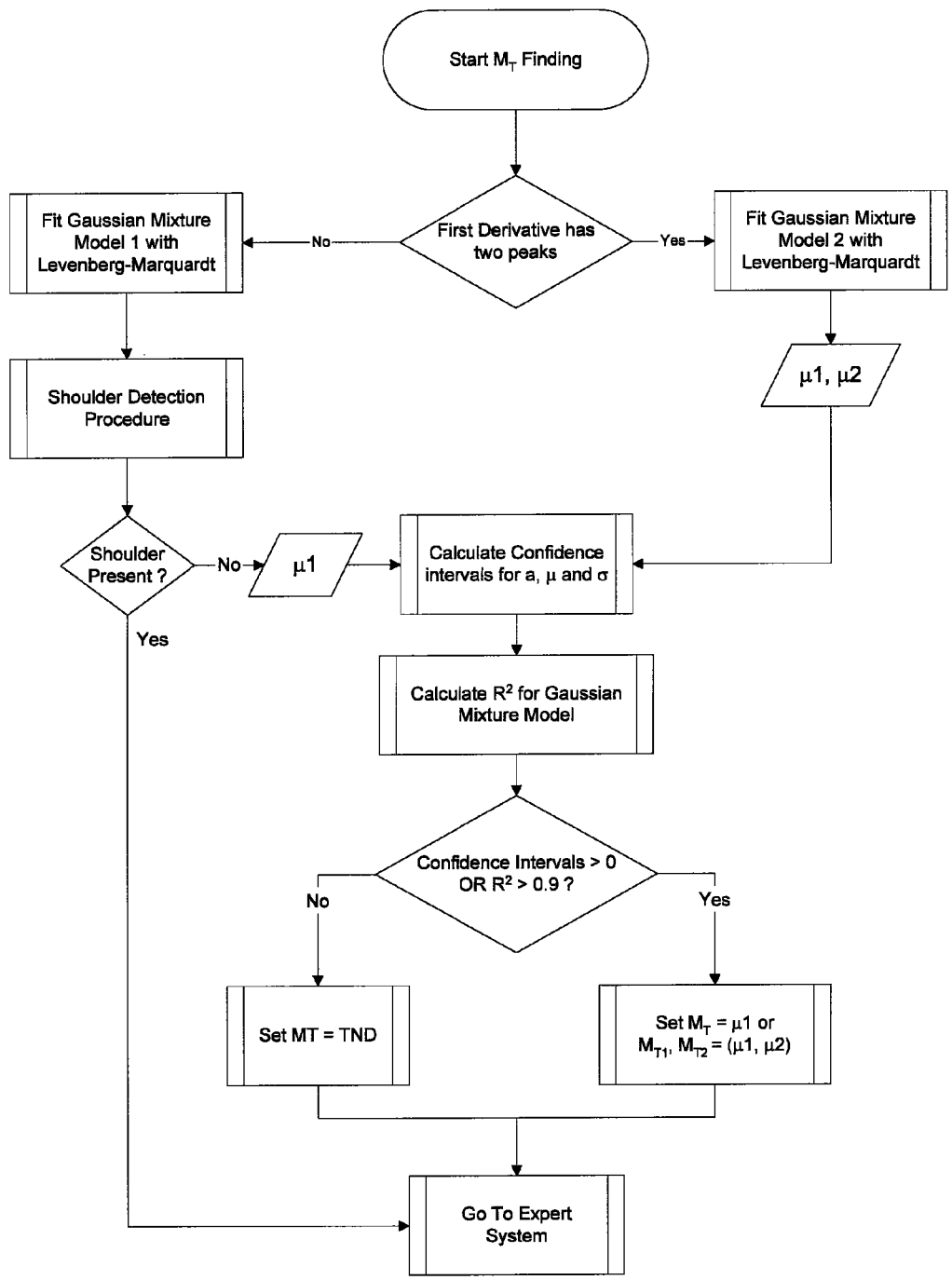
Figure 5: Major Processing Steps of the Equation-Less Melting Algorithm

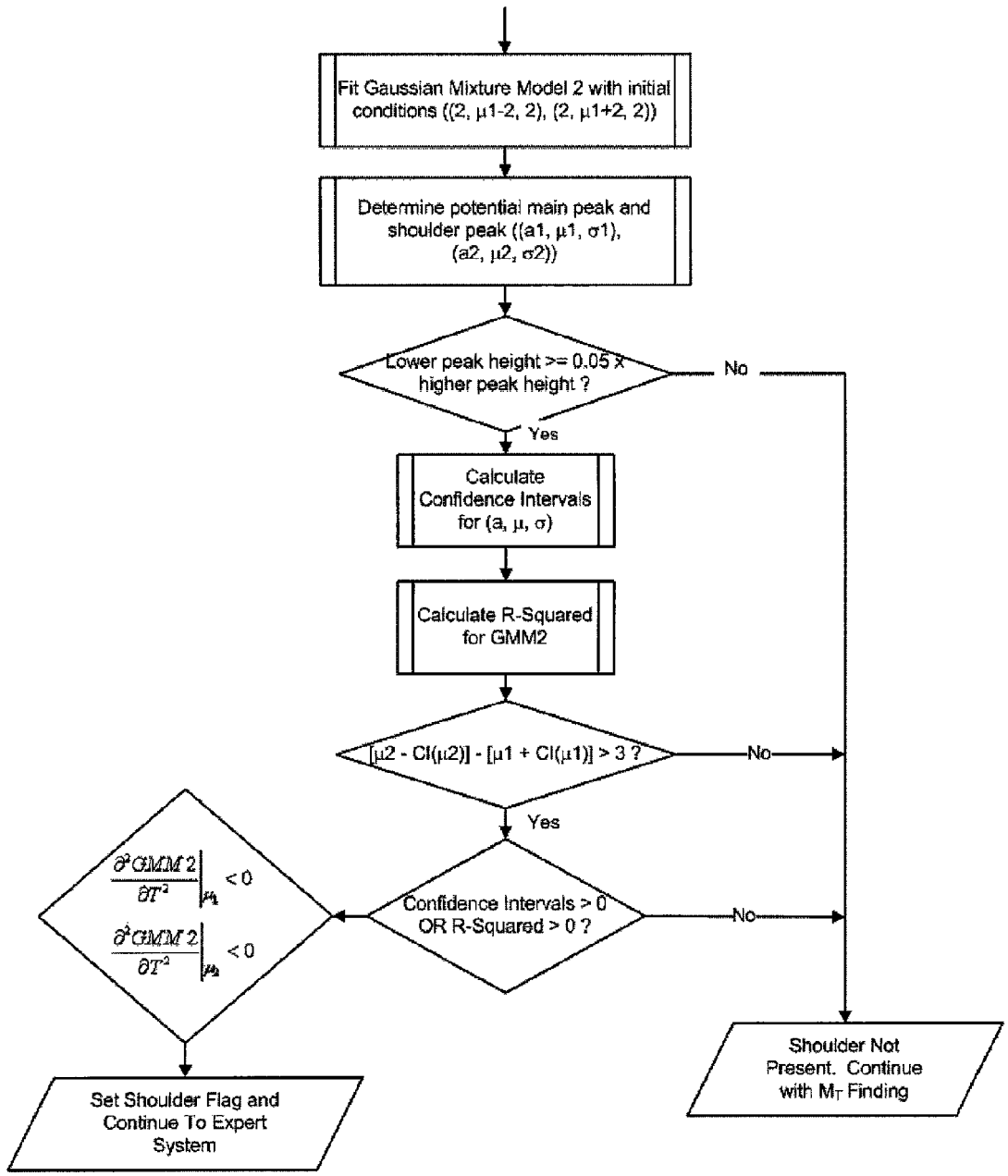
Figure 6: Major Processing Steps of the Equation-Less Melting Algorithm

DETERMINATION OF MELTING TEMPERATURES OF DNA

RELATED APPLICATION

This application is a continuation-in-part of U.S. application Ser. No. 12/253,676, filed Oct. 17, 2008, the entire content of the above application is incorporated herein by reference.

BACKGROUND OF THE INVENTION

The present invention relates generally to processing data representing melt characteristics of oligonucleotides, and more particularly to systems and methods for determining one or more melting temperatures for an oligonucleotide sample based on melt curve data.

Determination of DNA melting temperatures, usually performed directly after a PCR experiment, is an important method to distinguish genotypes. For example, recently discussed in the literature is the use of examining the KRAS gene to determine which patients might be candidates for a treatment for non-small cell lung cancer. Patients whose KRAS gene is of a wild-type would benefit from the treatment, whereas if the patient had a mutant variation of this gene, the treatment would be of no benefit. As these treatments often have major side effects, it is very important to determine the patient's correct genotype. The use of a melting KRAS assay can help distinguish the genotype of the patient.

Therefore it is desirable to provide systems and methods that accurately and efficiently determine the melting temperature of a DNA sample.

BRIEF SUMMARY OF THE INVENTION

The present invention provides systems and method for determining melting temperatures, Tm, for oligonucleotides based on melt curve data.

In various embodiments, numerical determinations of the first derivatives of a melt curve data set are made. A model function, such as a Gaussian Mixture Model (GMM) function, with parameters determined using a Levenberg-Marquardt (LM) regression process is used to find an approximation to the first derivative curve. The maximum values of the numerically determined first derivative values are used as initial conditions for parameters of the model function. The determined parameters provide fractional melting temperature values, which can be returned, for example, displayed or otherwise used for further processing.

According to one aspect of the present invention, a computer-implemented method of determining a melting temperature, Tm, of DNA is provided. The method typically includes receiving a dataset representing a melt curve for a DNA sample, the dataset including a plurality of data points each having a pair of coordinate values. The method also typically includes numerically determining first derivative values for data points of the melt curve, determining a baseline for the first derivative values, subtracting out the baseline from the first derivative values to produce modified first derivative values, and determining a first maximum value of the modified first derivative values. The method also typically includes outputting said maximum value, wherein said initial condition represent a melting temperature Tm of the DNA sample. The method can further typically comprise the steps of calculating an approximation of a curve that fits the modified first derivative values by applying a Levenberg-Marquardt (LM) regression process to a Gaussian Mixture Model function to determine one or more parameters of the function, wherein said parameters include initial conditions, and wherein the first maximum value is used as an initial condition for a first parameter, and outputting the first parameter, wherein the determined first parameter represents a melting temperature, Tm, of the DNA sample. In certain aspects, the method further includes determining whether the first derivative values includes a shoulder value proximal to the first maximum value.

According to another aspect of the present invention, a computer readable medium is provided that stores code for controlling a processor to determine a melting temperature, Tm, of DNA. The stored code typically includes instructions to receive a dataset representing a melt curve for a DNA sample, the dataset including a plurality of data points each having a pair of coordinate values, to numerically determine first derivative values for data points of the melt curve, to determine a baseline for the first derivative values, to subtract out the baseline from the first derivative values to produce modified first derivative values, and to determine a first maximum value of the modified first derivative values. The code also typically includes instructions to output the first maximum value, wherein said first maximum value represent a melting temperature Tm of the DNA sample. The code also typically includes instructions to calculate an approximation of a curve that fits the modified first derivative values by applying a Levenberg-Marquardt (LM) regression process to a Gaussian Mixture Model function to determine one or more parameters of the function, wherein said parameters include initial conditions, and wherein the first maximum value is used as an initial condition for a first parameter, and to output the first parameter, wherein the determined first parameter represents a melting temperature, Tm, of the DNA sample.

According to yet another aspect of the present invention, a kinetic Polymerase Chain Reaction (PCR) system is provided that typically includes a kinetic PCR analysis module that generates a melt curve dataset representing a DNA melt curve, the dataset including a plurality of data points, each having a pair of coordinate values, and an intelligence module adapted to process the melt curve dataset to determine a Tm value. The intelligence module typically determines a Tm value by numerically determining first derivative values for data points of the melt curve, by determining a baseline for the first derivative values, by subtracting out the baseline from the first derivative values to produce modified first derivative values, and by determining a first maximum value of the modified first derivative values. The intelligence module also typically determines a Tm value by using the determined first maximum value of the modified first derivative as the Tm value and outputting said Tm value. The intelligence module also typically determines a Tm value by calculating an approximation of a curve that fits the modified first derivative values by applying a Levenberg-Marquardt (LM) regression process to a Gaussian Mixture Model function to determine one or more parameters of the function, wherein said parameters include initial conditions, and wherein the first maximum value is used as an initial condition for a first parameter, and by outputting the first parameter, wherein the determined first parameter represents a melting temperature, Tm, of the DNA sample.

In certain aspects, a Gaussian Mixture Model includes an expression of the form:

$$GMM_1 = \text{Exp}(-a_1) \cdot \text{Exp}\left(-\frac{1}{2}\left(\frac{x-\mu_1}{\sigma_1}\right)^2\right),$$

wherein $\mu_1$ is the first parameter, and wherein $a_1$ and $\sigma_1$ are additional parameters.

In certain aspects, a second maximum value of the modified first derivative values is determined, wherein the second maximum value is used as an initial condition for a second parameter, and wherein a Gaussian Mixture Model includes an expression of the form:

$$GMM_2 = \text{Exp}(-a_1) \cdot \text{Exp}\left(-\frac{1}{2}\left(\frac{x-\mu_1}{\sigma_1}\right)^2\right) + \text{Exp}(-a_2) \cdot \text{Exp}\left(-\frac{1}{2}\left(\frac{x-\mu_2}{\sigma_2}\right)^2\right),$$

wherein $\mu_1$ is the first parameter, $\mu_2$ is the second parameter and wherein $a_1$, $\sigma_1$, $a_2$ and $\sigma_2$ are additional parameters.

In certain aspects, a third maximum value of the modified first derivative values is determined, wherein the third maximum value is used as an initial condition for a third parameter, and wherein a Gaussian Mixture Model includes an expression of the form:

$$GMM_3 = \text{Exp}(-a_1) \cdot \text{Exp}\left(-\frac{1}{2}\left(\frac{x-\mu_1}{\sigma_1}\right)^2\right) +$$
$$\text{Exp}(-a_2) \cdot \text{Exp}\left(-\frac{1}{2}\left(\frac{x-\mu_2}{\sigma_2}\right)^2\right) + \text{Exp}(-a_3) \cdot \text{Exp}\left(-\frac{1}{2}\left(\frac{x-\mu_3}{\sigma_3}\right)^2\right)$$

wherein $\mu_1$ is the first parameter, $\mu_2$ is the second parameter, $\mu_3$ is the third parameter and wherein $a_1$, $\sigma_1$, $a_2$, $\sigma_2$ $a_3$ and $\sigma_3$ are additional parameters.

In certain aspects, a fourth maximum value of the modified first derivative values is determined, wherein the fourth maximum value is used as an initial condition for a fourth parameter, and wherein a Gaussian Mixture Model includes an expression of the form:

$$GMM_4 = \text{Exp}(-a_1) \cdot \text{Exp}\left(-\frac{1}{2}\left(\frac{x-\mu_1}{\sigma_1}\right)^2\right) + \text{Exp}(-a_2) \cdot \text{Exp}\left(-\frac{1}{2}\left(\frac{x-\mu_2}{\sigma_2}\right)^2\right) +$$
$$\text{Exp}(-a_3) \cdot \text{Exp}\left(-\frac{1}{2}\left(\frac{x-\mu_3}{\sigma_3}\right)^2\right) + \text{Exp}(-a_4) \cdot \text{Exp}\left(-\frac{1}{2}\left(\frac{x-\mu_4}{\sigma_4}\right)^2\right)$$

wherein $\mu_1$ is the first parameter, $\mu_2$ is the second parameter, $\mu_3$ is the third parameter, $\mu_4$ is the fourth parameter and wherein $a_1$, $\sigma_1$, $a_2$, $\sigma_2$, $a_3$, $\sigma_3$, $a_4$ and $\sigma_4$ are additional parameters.

Reference to the remaining portions of the specification, including the drawings and claims, will realize other features and advantages of the present invention. Further features and advantages of the present invention, as well as the structure and operation of various embodiments of the present invention, are described in detail below with respect to the accompanying drawings. In the drawings, like reference numbers indicate identical or functionally similar elements.

BRIEF DESCRIPTION OF THE DRAWINGS

FIG. 1 illustrates an example of a melt curve.

FIG. 2 illustrates a first derivative curve for the melt curve of FIG. 1.

FIG. 3 shows the derivative curve of FIG. 2 after baseline subtraction.

FIG. 4 illustrates a process for determining melting temperature(s) according to one embodiment.

FIG. 5 illustrates a Melting Temperature computation process according to one embodiment.

FIG. 6 illustrates a shoulder detection process according to one embodiment.

DETAILED DESCRIPTION OF THE INVENTION

Figure 7A:
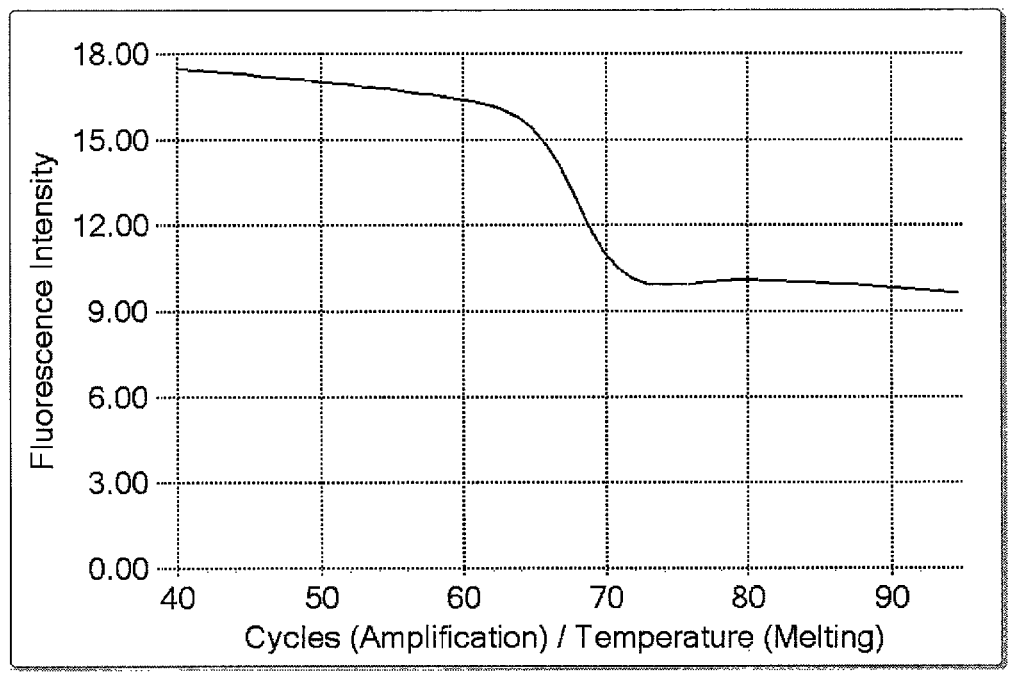
FIGS. 7a and 7b show an example of a raw data curve and a melting curve, respectively, in the case of a single melting peak.

The present invention provides systems and methods for determining melting temperatures, Tm, for DNA.

The present invention provides systems and methods for determining a melting temperature by analyzing data representing a melt curve. In certain aspects, numerical determinations of the first derivatives of a melt curve data set are made. A Gaussian Mixture Model (GMM) function with parameters determined using a Levenberg-Marquardt (LM) regression process is used to find an approximation to the first derivative curve. The maximum values of the numerically determined first derivative values are used as initial conditions for parameters of the GMM function. The determined parameters provide fractional melting temperature, Tm, values. The Tm value(s) are then returned and may be displayed or otherwise used for further processing.

One example of a melt curve in the context of a PCR process is shown in FIG. 1. As shown in FIG. 1, data for a typical melt curve can be represented in a two-dimensional coordinate system, for example, with temperature defining the x-axis and an indicator of accumulated polynucleotide defining the y-axis. Typically, the indicator of accumulated polynucleotide is a fluorescence intensity value as the use of fluorescent markers is perhaps the most widely used labeling scheme. However, it should be understood that other indicators may be used depending on the particular labeling and/or detection scheme used. Examples of other useful indicators of accumulated signal include luminescence intensity, chemiluminescence intensity, bioluminescence intensity, phosphorescence intensity, charge transfer, voltage, current, power, energy, temperature, viscosity, light scatter, radioactive intensity, reflectivity, transmittance and absorbance.

General Process Overview

Consider a typical melt curve as shown in FIG. 1. It is desired to obtain one or more melting temperatures from the data represented in FIG. 1. According to one embodiment, a process 100 for determining a melting temperature can be described briefly with reference to FIG. 4. In step 110, an experimental data set representing the melt curve is received or otherwise acquired. An example of a plotted melt curve data set is shown in FIG. 1, where the y-axis and x-axis represent fluorescence intensity and temperature, respectively, for a melt curve. In certain aspects, the data set should include data that is continuous and equally spaced along an axis.

In the case where process 100 is implemented in an intelligence module (e.g., processor executing instructions) resident in a PCR device such as a thermocycler, the data set may be provided to the intelligence module in real time as the data is being collected, or it may be stored in a memory unit or buffer and provided to the intelligence module after the experiment has been completed. Similarly, the data set may be provided to a separate system such as a desktop computer system or other computer system, via a network connection (e.g., LAN, VPN, intranet, Internet, etc.) or direct connection (e.g., USB or other direct wired or wireless connection) to the acquiring device, or provided on a portable medium such as a CD, DVD, floppy disk or the like. In certain aspects, the data set includes data points having a pair of coordinate values (or a 2-dimensional vector). For melt data, the pair of coordinate values typically represents the temperature and the fluorescence intensity value. After the data set has been received or acquired in step 110, the data set may be analyzed to determine the melting temperature(s).

In step 120, the data is numerically processed to determine derivative values. The melting temperatures for these curves is obtained by finding the (fractional) temperature value (x-axis) corresponding to the maximum of the first derivative (y-axis) of the fluorescence intensity with respect to temperature. Using the data shown in FIG. 1, corresponding graphs for the first derivative is shown in FIG. 2. In one embodiment, baseline subtraction is performed on the derivative curve data to produce modified derivative data. In one embodiment, baseline subtraction is performed by first defining "MedianLeft" as the median of the fluorescent values of the first five points in FIG. 2, then defining "MedianRight" as the median of the fluorescent values of the last five points in FIG. 2. A straight line is then defined connecting the "MedianLeft" point (x, y) in FIG. 2 with the "MedianRight" point (x, y). The slope and intercept of this straight line is then subtracted from all coordinate pairs. FIG. 3 shows the derivative curve after baseline subtraction.

In one embodiment, derivatives are obtained by use of the Savitzky-Golay (SG) method. [See A. Savitzky and Marcel J. E. Golay (1964). Smoothing and Differentiation of Data by Simplified Least Squares Procedures Analytical Chemistry, 36: 1627-1639 and Press, W. H., et al. "Numerical Recipes in C, 2nd Ed.," Savitzky-Golay Smoothing Filters, Section 14.8, 650-655.]. A SG-2-2-2 configuration (meaning 2 points to the left, 2 points to the right, and 2nd degree polynomial) is used, in one embodiment, to calculate the first derivative of the raw melting data curve. In general, other configurations of the SG method may be used, for example, SG-1-1-2 to SG-50-50-2. More generally, SG-x-y-z may be used where x and y are numbers from 1 to 50 and z is a number from 1 to 5.

Scale Invariant Forms of Derivatives

In certain embodiments, alternative methods are used to calculate derivatives in order to allow the melting temperature to be scale-invariant. Scale invariant means that if fluorescence values are multiplied by a constant, the resulting Tm value(s) are unchanged.

According to one method, the fluorescence value is divided by the mean fluorescence value before calculation of the derivative melting curve, e.g., y is replaced by:

$$y/y_{mean}, \text{ where } y_{mean} = \frac{1}{n}\sum_{i=1}^{n} y_i. \tag{1}$$

According to another method, the fluorescence value is divided by the (maximum fluorescence-minimum fluorescence) before calculation of the derivative melting temperatures.

According to another method, the derivative of the fluorescence value is divided by the fluorescence value before calculation of the melting temperatures.

According to yet another method, the derivative of the fluorescence value is divided by the mean derivative of the fluorescence value before calculation of the melting temperatures.

According to still another method, the derivative of the fluorescence value is divided by the (maximum-minimum) derivative of the fluorescence value before calculation of the melting temperatures.

Returning to FIG. 4, in step 130, a number of peaks in the first derivatives data is determined. In one embodiment, a local maximization process is used to determine zero, one, two three or four peaks in the first derivatives data as will be discussed in more detail below. The raw derivatives data may be used, or the baseline subtracted derivatives data may be used.

In one embodiment, fractional Tm values are determined in step 140. To find the maximum values of the curves, for example as shown in FIG. 2 or 3, in one embodiment, a Gaussian Mixture Model is fit to the data. The mean of the Gaussian Mixture Model corresponds to the maximum, and hence the Tm value. In one embodiment, a curve fit is done by calculating an approximation of a curve that fits the determined first derivative values, or modified (baseline subtracted) derivative values, by applying a regression process to a Gaussian Mixture Model function to determine one or more parameters of the function. In certain aspects, a Levenberg-Marquardt regression process is used. In one embodiment, for the case of a single peak, a Gaussian Mixture Model for one peak is used as shown in equation (2). If two peaks are present, a Gaussian Mixture Model for two peaks is used as shown in equation (3). If three peaks are present, a Gaussian Mixture Model for three peaks can be used as shown in equation (4). If four peaks are present, a Gaussian Mixture Model for four peaks can be used as shown in equation (5). The regressed values for the coefficients $\mu_1$ or ($\mu_1$, $\mu_2$) correspond to the Tm values for one and two peaks respectively. Gaussian Mixture Models are used in one embodiment, rather than taking additional derivatives to find the maximum, as higher order derivatives ($3^{rd}$, and $4^{th}$) can become unstable.

$$GMM_1 = \text{Exp}(-a_1) \cdot \text{Exp}\left(-\frac{1}{2}\left(\frac{x-\mu_1}{\sigma_1}\right)^2\right) \tag{2}$$

$$GMM_2 = \tag{3}$$
$$\text{Exp}(-a_1) \cdot \text{Exp}\left(-\frac{1}{2}\left(\frac{x-\mu_1}{\sigma_1}\right)^2\right) + \text{Exp}(-a_2) \cdot \text{Exp}\left(-\frac{1}{2}\left(\frac{x-\mu_2}{\sigma_2}\right)^2\right)$$

$$GMM_3 = \text{Exp}(-a_1) \cdot \text{Exp}\left(-\frac{1}{2}\left(\frac{x-\mu_1}{\sigma_1}\right)^2\right) + \tag{4}$$
$$\text{Exp}(-a_2) \cdot \text{Exp}\left(-\frac{1}{2}\left(\frac{x-\mu_2}{\sigma_2}\right)^2\right) + \text{Exp}(-a_3) \cdot \text{Exp}\left(-\frac{1}{2}\left(\frac{x-\mu_3}{\sigma_3}\right)^2\right)$$

$$GMM_4 = \qquad (5)$$
$$\text{Exp}(-a_1) \cdot \text{Exp}\left(-\frac{1}{2}\left(\frac{x-\mu_1}{\sigma_1}\right)^2\right) + \text{Exp}(-a_2) \cdot \text{Exp}\left(-\frac{1}{2}\left(\frac{x-\mu_2}{\sigma_2}\right)^2\right) +$$
$$\text{Exp}(-a_3) \cdot \text{Exp}\left(-\frac{1}{2}\left(\frac{x-\mu_3}{\sigma_3}\right)^2\right) + \text{Exp}(-a_4) \cdot \text{Exp}\left(-\frac{1}{2}\left(\frac{x-\mu_4}{\sigma_4}\right)^2\right)$$

It should be appreciated that other models/functions could be used instead of a Gaussian Mixture Model as would be apparent to one skilled in the art. Examples of other models include Beta, Binomial, Cauchy, Chi, ChiSquare, Exponential, Extreme Value, FRatio, Gamma, Gumbel, Laplace, Logistic, Maxwell, Pareto, Rayleigh, StudentT, and Weibull models.

It is to be understood that the above embodiment can be applied with first derivative data comprising more than two peaks. In this case, the initial estimates (regressed values) for the coefficients $\mu_1$, $\mu_2$, $\mu_3$, $\mu_4$ by the local maximum corresponds to the final melting temperature.

In one embodiment, the Levenberg-Marquardt (LM) method is used to curve fit equation (2) (or equation (3), equation (4), equation (5)). Details of this method can be found in the reference [Moré, J. J., "The Levenberg-Marquardt Algorithm, Implementation and Theory," *Numerical Analysis*, ed. Watson, G. A. Lecture Notes in Mathematics 630, Springer-Verlag, 1977, incorporated by reference herein]. It should be appreciated that other regression methods as are well known may be used. In general, the LM regression method includes an algorithm that requires various inputs and provides output. In one aspect, the inputs include a data set to be processed, a function (e.g., Gaussian Mixture Model) that is used to fit the data, and an initial guess for the parameters or variables of the function. The output includes a set of one or more parameters for the function that minimizes the sum of the squares of the distance between the function and the data set. It should be appreciated that other regression processes as would be apparent to one skilled in the art may be used.

One feature of the Levenberg-Marquardt method is that it requires good estimates of the parameter values prior to performing the regression. For the parameters $a_1$ (or $a_1, a_2, a_3, a_4$) and $\sigma_1$ (or $\sigma_1, \sigma_2, \sigma_3, \sigma_4$) the initial conditions can be set equal to a constant (e.g., 1 or 2) in all cases. These parameters are generally not sensitive and will generally converge regardless of the initial conditions used. The parameters $\mu_1$ (or $\mu_1, \mu_2, \mu_3, \mu_4$) may require more accurate initial conditions that should be determined for each curve. In one embodiment, a windowing method is used to calculate initial conditions for the parameters $\mu_1$ (or $\mu_1, \mu_2, \mu_3, \mu_4$) as described in more detail below.

In optional step 150, one or more expert system checks are performed to assess whether the results are valid as will be discussed in more detail below. For example, if implemented, an expert system check may determine that the determined result is invalid.

In step 160, the Tm value(s) are returned, e.g., for display or further processing. Graphical displays may be rendered with a display device, such as a monitor screen or printer, coupled with the system that performed the analysis of FIG. 4, or data may be provided to a separate system for rendering on a display device.

In some embodiments, the $R^2$ statistic and/or confidence (e.g., 95% confidence) intervals are calculated for the $GMM_1$, $GMM_2$, $GMM_3$ $GMM_4$ parameters. These values assess the quality of the curve fit and may be used in an Expert System (described below) to help determine whether the calculated Tm values are valid, invalid, or zero (no sample present). These values may also be displayed in step 160.

Determination of Maximum in Curves

In one embodiment, a windowing process is used on the data set to determine initial conditions for the parameters $\mu_1$, $\mu_2$, $\mu_3$, $\mu_4$. The following windowing process is described for a first derivative comprising up to two peaks. Nevertheless, as mentioned above, it is to be understood that this windowing process can be applied to first derivative data presenting up to four peaks without departing from the scope of the invention. In one embodiment, the windowing process searches for potential local maxima by using the following procedure:

1. Starting at the first point, examine the first several (e.g., five) points (points 1-5) of the data set.
2. If the middle y-Point is not the maximum in these five points, then there is no potential maximum in these five points. If the middle y-point is the maximum of these five points and it has a value greater than 0 (to avoid adding the middle points of a longer sequence of points with an exact value of 0 into the set of potential maxima), then there is a potential maximum. Add this point to the set of potential maxima S.
3. Advance the sliding window by one point (e.g., now points 2-6), and repeat the process described in item 2, again accepting only maxima at index 3 of these five points. Continue this process throughout the entire data set.
4. Examine the result set S of possible maxima, representing the set of possible maxima at index 3, and find the maximum data point in this set S of possible maxima (Smax).
5. If Smax is equal or less than a MaxNoise Input Parameter (a noise parameter that may be input by a user, or automatically determined), there is no peak in the curvature data.
6. Keep the remaining possible maximum data points from this set S, providing that they are greater than Smax×a RelativeMin Input Parameter and greater than an AbsoluteMin Input Parameter.
7. If there is only one data point left, there is only one peak, and the curve has only one maximum. Define this single peak as $pk_1$. If there are two data points left, then this represents a curve with two maxima. If there are more than two peaks, take the two peaks with the highest values of the data set S and return the peak with the lower cycle number of these two as $pk_1$ and the peak with the higher cycle number as $pk_2$.
8. The initial condition for $\mu_1$ is then $pk_1$ and the initial condition for $(\mu_1, \mu_2)$ is $(pk_1, pk_2)$ Melting Temperature Computation A Melting Temperature computation according to one embodiment is illustrated in FIG. 5. In step 210, a determination is made as to whether the first derivative data set includes one or two (or three, four) peaks. If the first derivative of the melting data set is identified as having a single peak, in step 220, the maximum of the melting curve is found by a nonlinear regression (e.g., using the Levenberg-Marquardt method or other regression method) of the single component Gaussian function as described in equation (2). The initial conditions are given by the local maxima search. If the first derivative of the melting data set is identified as having two peaks (or three, four), in step 230, both local maxima of the melting curve are found by a nonlinear regression (e.g., using the Levenberg-Marquardt method) of the double component Gaussian function as described in equation (3), and the parameters $\mu_1$, $\mu_2$ (or $\mu_3$ and $\mu_4$) (corresponding to Tm1, Tm2, or Tm3 and Tm4) are returned. The initial conditions are given by the local maxima search. It should be appreciated that even if FIG. 5 shows a melting temperature computation for one or two peaks, the same melting temperature computation used for two peaks can also be used for three and four peaks.

In step 240, a shoulder detection process determines whether a shoulder is present for the single derivative peak situation according to one embodiment. If two (or three, four) peaks are found in the MELT algorithm, no further action is taken. If instead, if one peak is found, it might be possible that a shoulder is present on this peak. Details of a shoulder detection process according to one embodiment are discussed below. If no shoulder is detected, $\mu_1$ (corresponding to Tm1) is returned. In step 250 confidence intervals are determined for the various parameters. In step 260, an $R^2$ value is calculated for the Gaussian Mixture Model used. In one embodiment, if the $R^2$ value of the GMM (or GMM2, GMM3, GMM4) fit is >0.9, or the confidence intervals for the parameters ($\mu_1$, $\sigma_1$), or ($\mu_1$, $\sigma_1$, $\mu_2$, $\sigma_2$, $\mu_3$, $\sigma_3$, $\mu_4$, $\sigma_4$) do not include zero, then the values of Tm1 (or Tm1, Tm2, Tm3, Tm4) are accepted in step 270. Otherwise, Tm1, (or Tm1, Tm2, Tm3, Tm4) are set as target not detected (TND) in step 280, and the optional Expert System in step 290 makes the final call of TND or Invalid.

Shoulder Detection

A shoulder detection process according to one embodiment is shown in FIG. 6. In step 310, a double component Gaussian model is fit to the same first derivative data using $a_{1,2}=2$, $\mu_{1,2}=m\pm2$, $\sigma_{1,2}=2$ as initial conditions, where m is the melting temperature of the single peak. In step 320, the potential main peak and shoulder (lower) peak are determined as above. In step 330, a determination is made as to whether the height of the lower peak is at least a certain percentage (e.g., 0.05 or more times the higher peak) of the higher peak. If not, a shoulder not present call is returned and Tm determination processing continues as per step 250 in FIG. 5. If so, in step 340, confidence intervals are determined for the various parameters and, in step 350, an $R^2$ value is determined for the GMM2 equation. In step 360, a determination is made as to whether the confidence intervals of the means are at least a certain number of degrees Centigrade apart from each other (e.g., 3 degrees or more). If not, a shoulder not present call is returned and Tm determination processing continues as per step 250 in FIG. 5. If so, in step 370, a determination is made as to whether the confidence intervals do not contain zero, or whether the $R^2$ value is greater than a threshold (e.g., 0.9). If not, a shoulder not present call is returned and Tm determination processing continues as per step 250 in FIG. 5. If so, in step 380, a determination of whether the second (2d) derivative of the double component Gaussian model (GMM2) evaluated at both $\mu_1$ and $\mu_2$ is negative. If so, a shoulder detected call is made.

Thus, assuming the LM-method converged, in one embodiment, a shoulder is detected if ALL of the following conditions hold true:

The first derivative data was identified to have exactly one local maximum.
The lower peak is at least 0.05 times the higher peak in height (e.g., using "exp(-a)").
The confidence intervals of the means are at least a 3 degrees Centigrade apart from each other.
The confidence intervals of $\mu_1$, $\mu_2$, $\sigma_1$ and $\sigma_2$ do not contain zero or $R^2$>0.9.
The second derivative of the double component Gaussian model (GMM2) evaluated at both $\mu_1$ and $\mu_2$ is negative.

In the case in which these conditions are fulfilled, a Shoulder Detection flag is raised. The above shoulder detection process is described in connection with FIG. 6 for a first derivative comprising one or two peaks. Nevertheless, as mentioned above, it should be understood that this shoulder detection process can be applied to first derivative data presenting up to four peaks without departing from the scope of the invention.

Expert System Checks

In one embodiment, one or more expert system checks are implemented in step 290 (FIG. 5). In one check, it is determined whether the median of all the entire melting curve data is >0. If this is false, then the result is reported as Invalid. In another check, it is determined whether the absolute value of the maximum of the Melt Peak fluorescent data is greater than the absolute value of the minimum of the Melt Peak fluorescent data. If this is false, then the result is reported as Invalid. In another check, it is determined whether the median of the raw fluorescence vs. temperature values from the first several (e.g., five) cycles is greater than the median of the raw fluorescence vs. temperature values from the last several (e.g., five) cycles. If this is false, then result is reported as Invalid. In yet another check, a second order polynomial is fit to the raw fluorescence vs. temperature data set. If the $R^2$ on this fit is greater than a threshold (e.g., 0.99), then no peaks are present and the result is reported as Target Not Detected (TND).

EXAMPLES

Figure 7B:
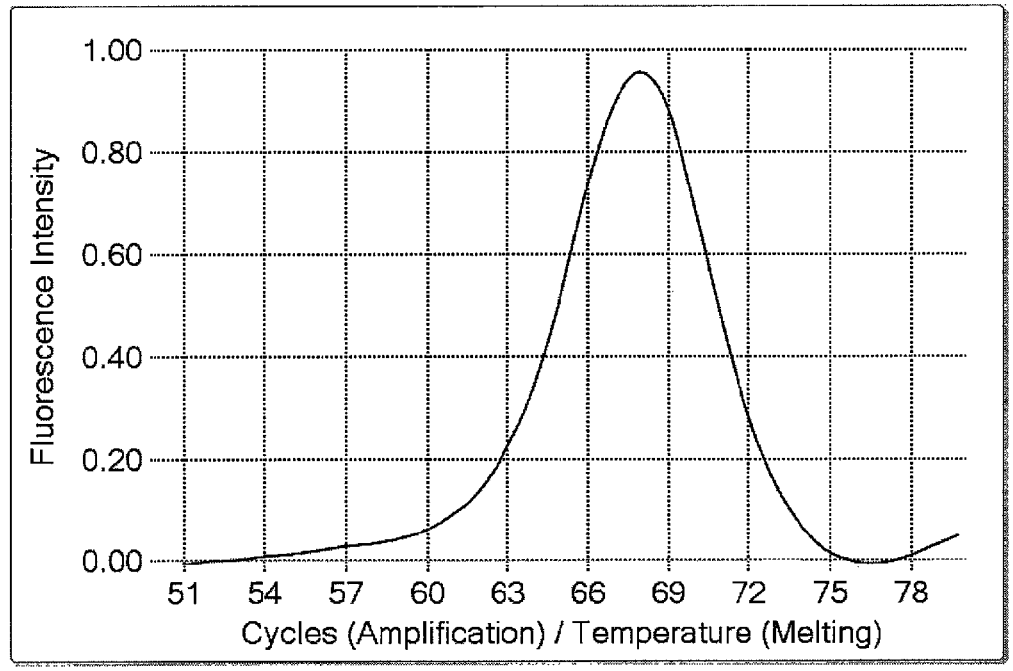

FIGS. 7a and 7b show a raw data curve and a melting curve, respectively, in the case of a single melting peak. The calculated melting temperature is Tm=67.8.

Figure 8A:
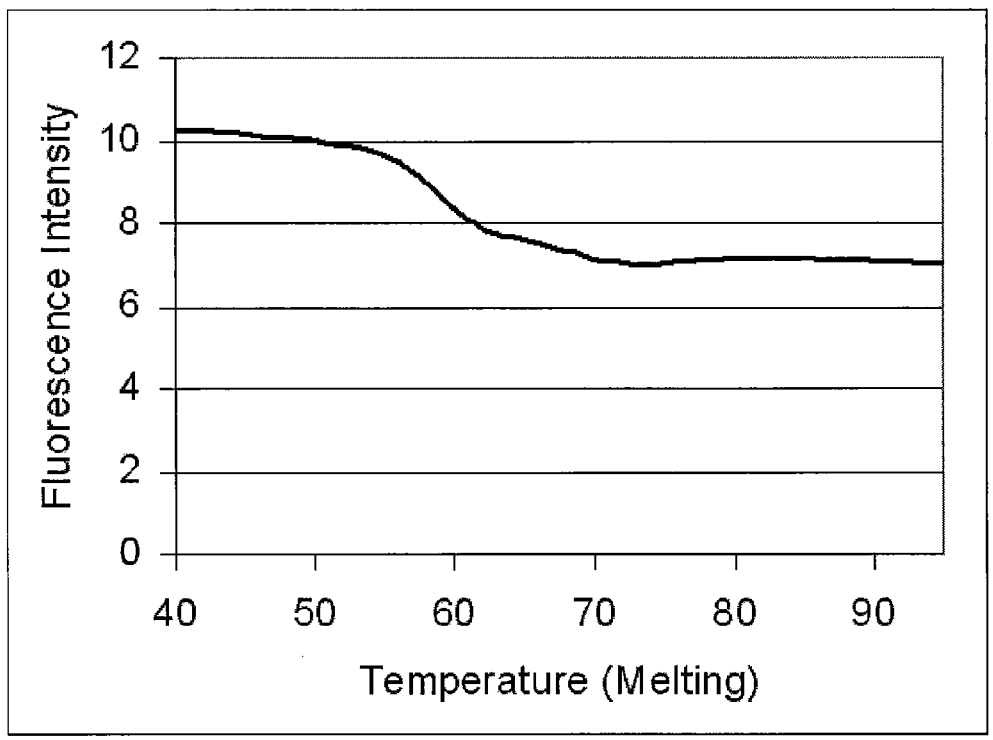
FIGS. 8a and 8b show an example of a raw data curve and a melting curve, respectively, in the case of a two melting peaks.
Figure 8B:
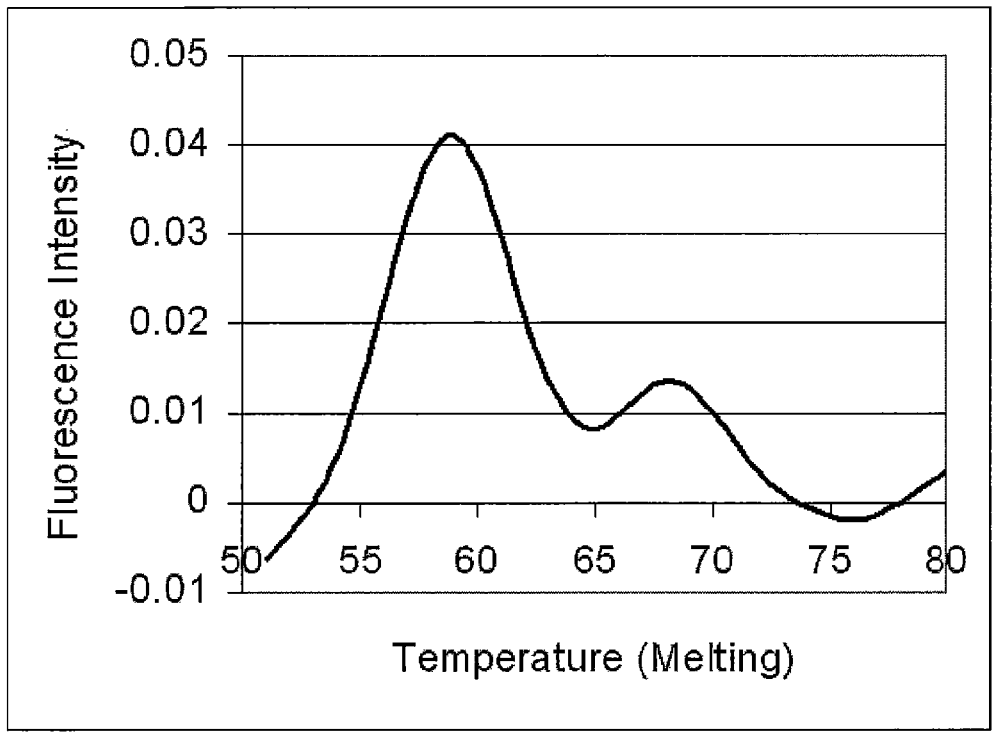

FIGS. 8a and 8b show a raw data curve and a melting curve, respectively, in the case of a two melting peaks. The calculated melting temperatures are Tm1=58.8 and Tm2=67.8.

Figure 9A:
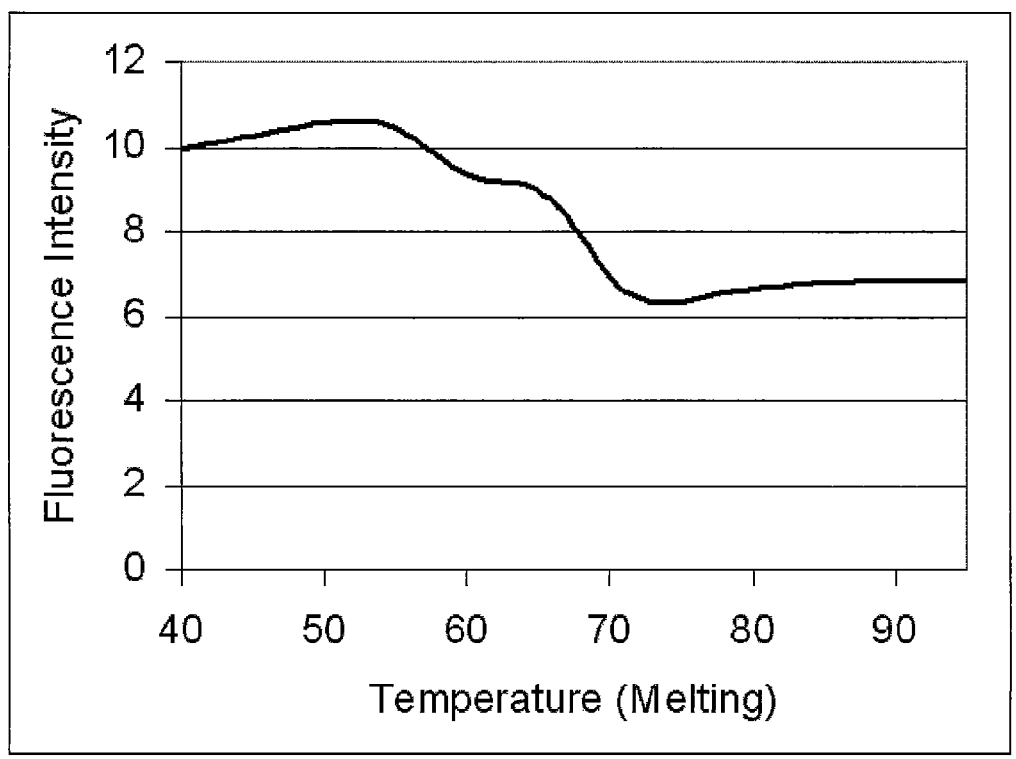
FIGS. 9a and 9b show an example of a raw data curve and a melting curve, respectively, in the case of a two melting peaks.
Figure 9B:
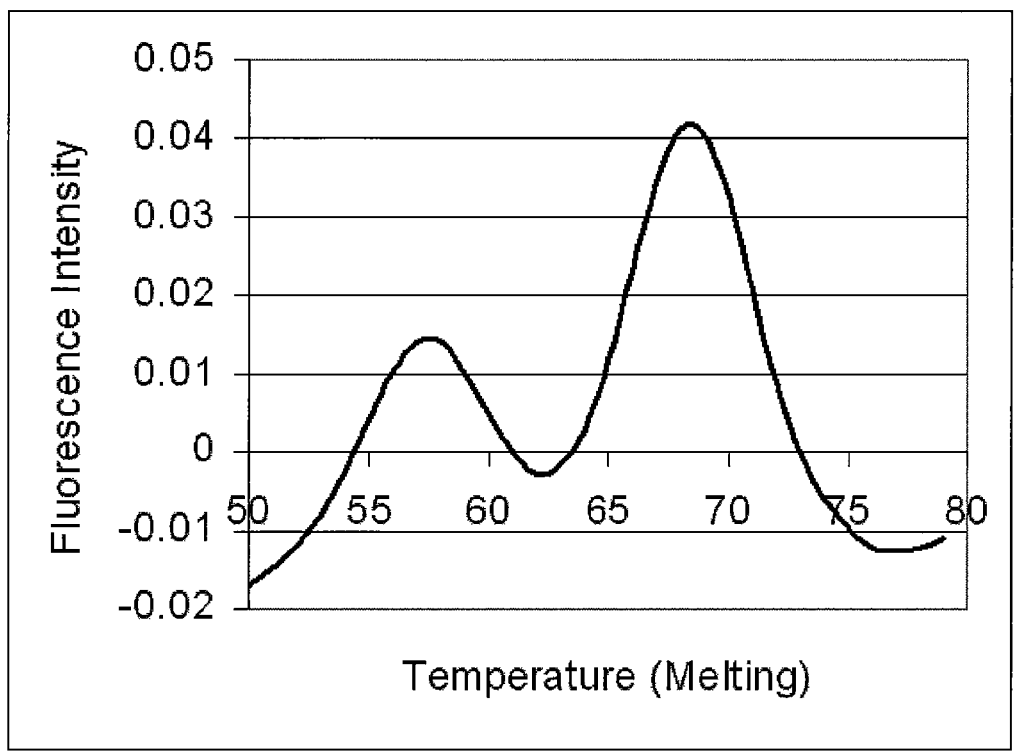

FIGS. 9a and 9b show a raw data curve and a melting curve, respectively, in the case of a two melting peaks. The calculated melting temperatures are Tm1=57.9 and Tm2=68.6.

Figure 10A:
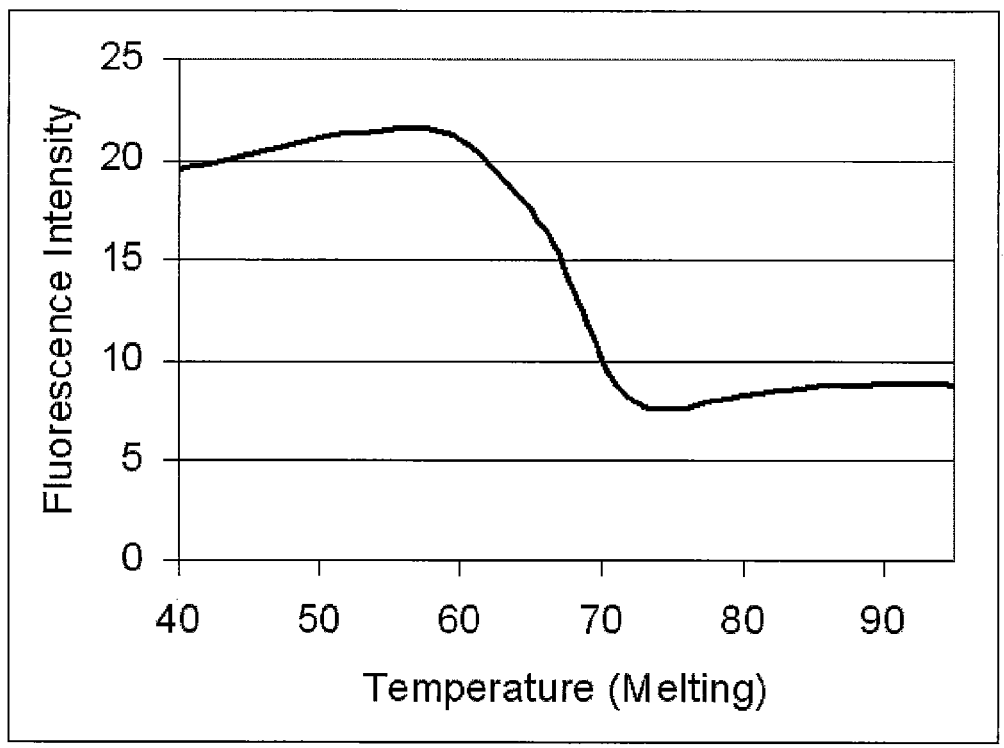
FIGS. 10a and 10b show an example of a raw data curve and a melting curve, respectively, in the case of a single melting peak plus a shoulder.
Figure 10B:
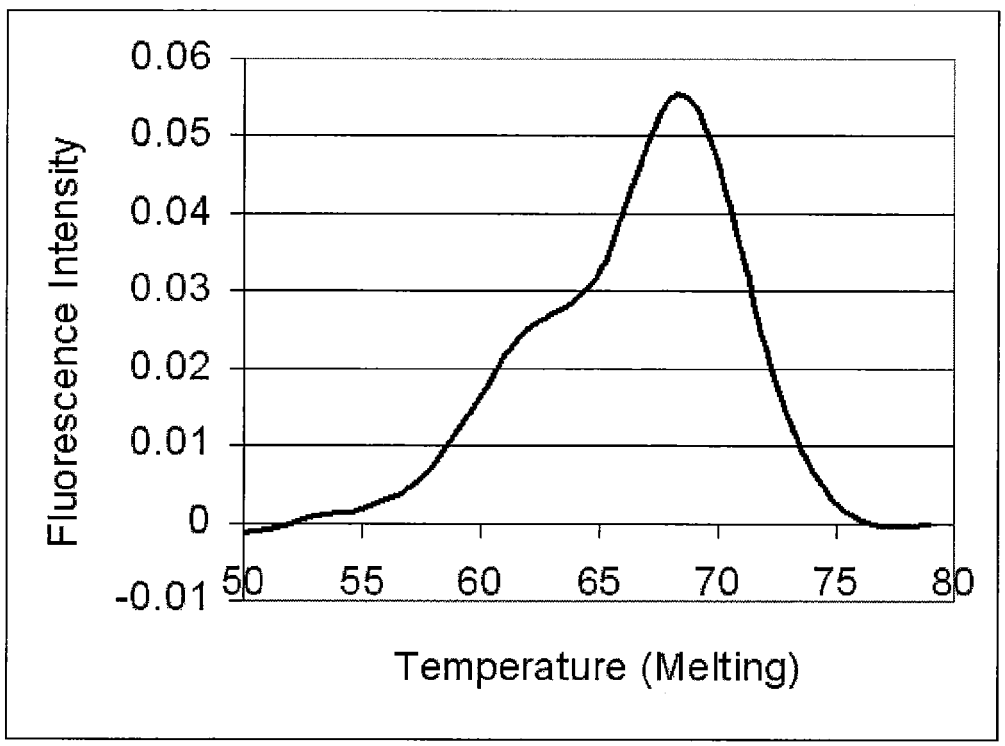

FIGS. 10a and 10b show a raw data curve and a melting curve, respectively, in the case of a single melting peak plus a shoulder. The calculated melting temperatures are Tm1=62.4 and Tm2=68.8.

Figure 11A:
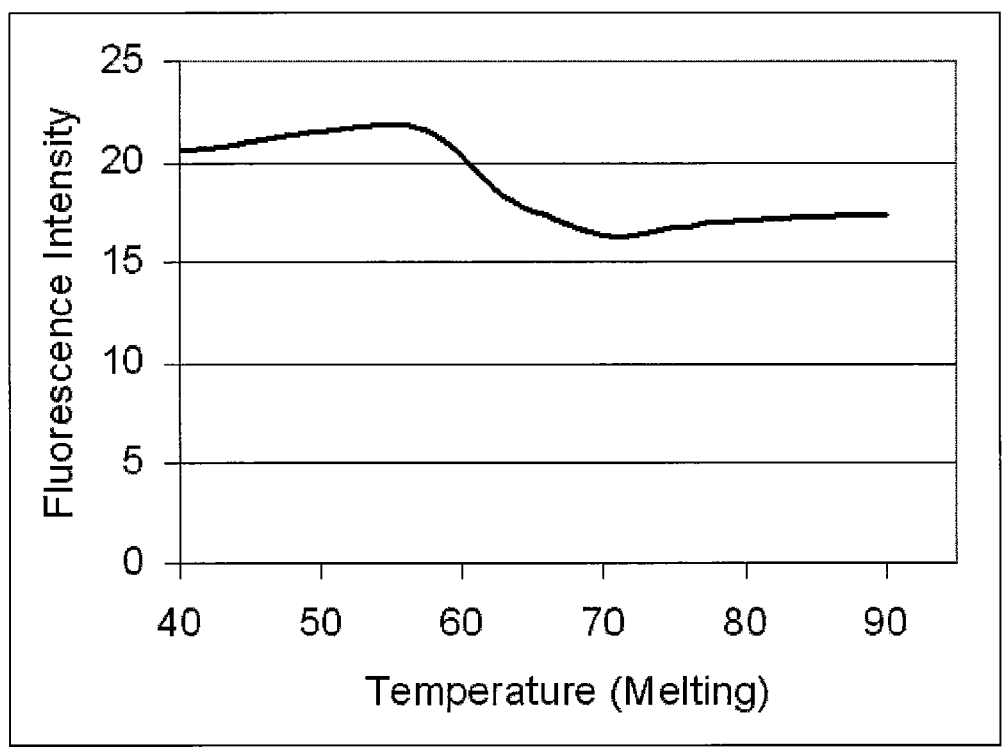
FIGS. 11a and 11b show an example of a raw data curve and a melting curve, respectively, in the case of a single melting peak plus a shoulder.
Figure 11B:
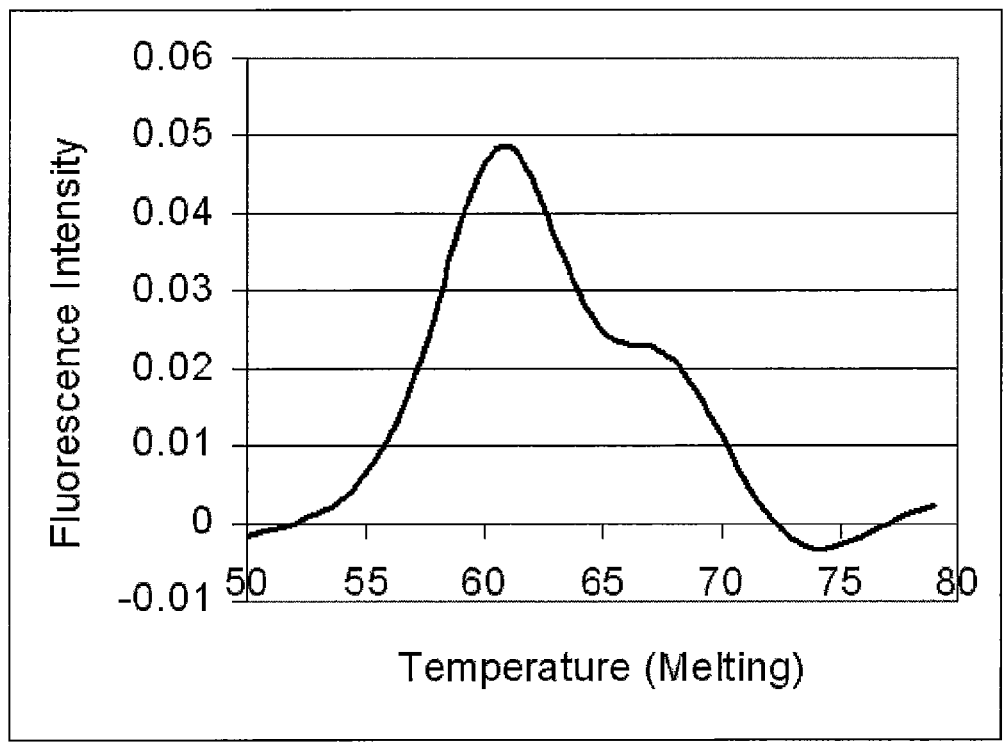

FIGS. 11a and 11b show a raw data curve and a melting curve, respectively, in the case of a single melting peak plus a shoulder. The calculated melting temperatures are Tm1=61.3 and Tm2=68.1.

Figure 12:
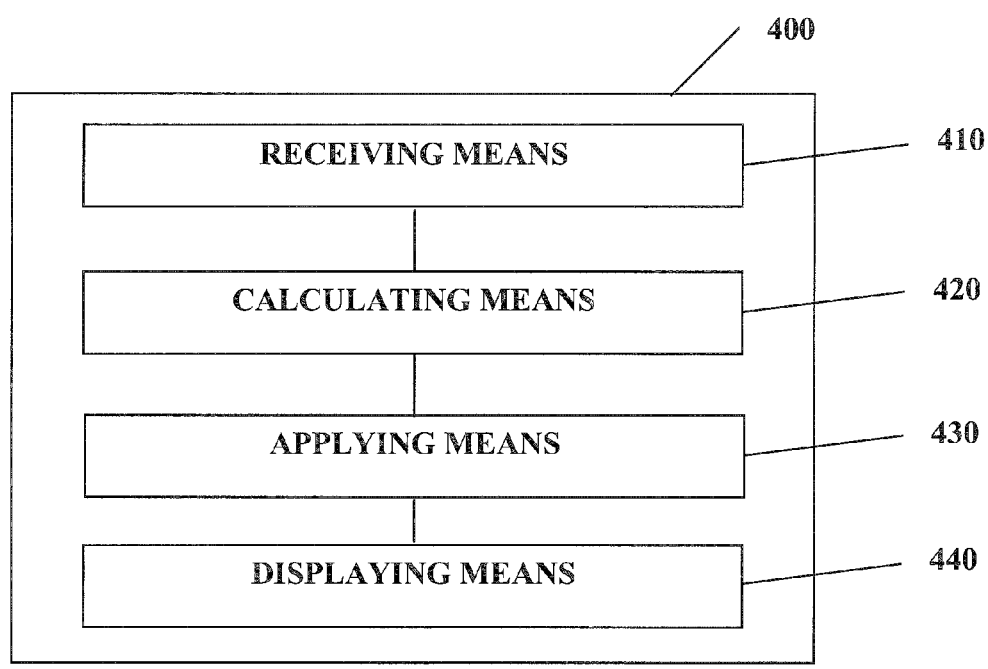
FIG. 12 shows a general block diagram explaining the relation between software and hardware resources that can be used to implement the processes and system of the invention.

FIG. 12 shows an example of a general block diagram explaining the relation between software and hardware resources that can be used to implement the processes and system of the invention on a computer.

Figure 13:
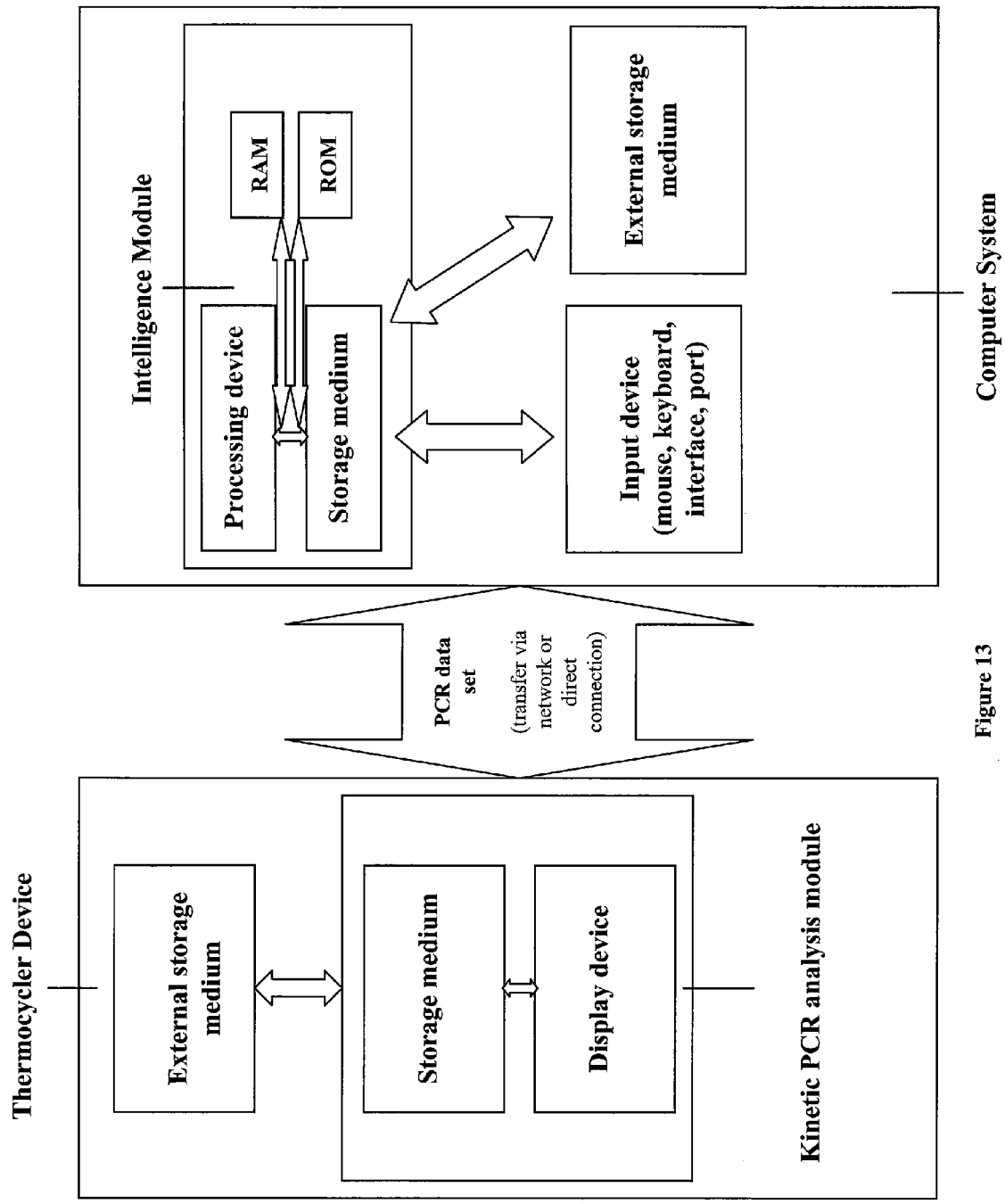
FIG. 13 illustrates the interaction between a thermocycler device and a computer system.

FIG. 13 shows and example of the interaction between a thermocycler device and a computer system.

It should be appreciated that the Tm determination processes, including the derivative and shoulder determination processes, may be implemented in computer code running on a processor of a computer system. The code includes instructions for controlling a processor to implement various aspects and steps of the Tm determination processes. The code is typically stored on a hard disk, RAM or portable medium such as a CD, DVD, etc. Similarly, the processes may be implemented in a PCR device such as a thermocycler, or other specialized device, including a processor executing instructions stored in a memory unit coupled to the processor. Code including such instructions may be downloaded to the device memory unit over a network connection or direct connection to a code source or using a portable medium as is well known.

One skilled in the art should appreciate that the Tm determination processes of the present invention can be coded using a variety of programming languages such as C, C++, C#, Fortran, Visualbasic™, etc., as well as applications such as Mathematica® which provide pre-packaged routines, functions and procedures useful for data visualization and analysis. Another example of the latter is Matlab®.

In a certain embodiment the Tm determination processes according to the invention can be implemented by using conventional personal computer systems including, but not limited to, an input device to input a data set, such as a keyboard, mouse, and the like; a display device to represent a specific point of interest in a region of a curve, such as a monitor; a processing device necessary to carry out each step in the method, such as a CPU; a network interface such as a modem, a data storage device to store the data set, a computer code running on the processor and the like. Furthermore, the processes may also be implemented in a PCR process such as according to the embodiments of claims 1 to 11 or in a PCR system such as according to the embodiments of claims 14 to 19.

An example of system according to claims 14 to 19 is displayed in FIGS. 12 and 13. FIG. 12 shows a general block diagram explaining the relation between software and hardware resources that may be used to implement the processes and system of the invention. The system depicted on FIG. 13 comprises a kinetic PCR analysis module which may be located in a thermocycler device and an intelligence module which is part of the computer system. The data sets (PCR data sets) are transferred from the analysis module to the intelligence module or vice versa via a network connection or a direct connection. The data sets may for example be processed according to the flowcharts as depicted on FIGS. 4, 5 and 6. These flowcharts may conveniently be implemented by a software stored on the hardware of a computer system for example according to the flowchart as depicted on FIG. 12. Referring to FIG. 12, computer system (400) may comprise receiving means (410) for example for receiving fluorescence data obtained during PCR reactions, calculating means (420) for processing said data according to the processes of the invention, applying means (430) for applying the result obtained by the calculation means, and displaying means (440) for displaying the results on a computer screen. FIG. 13 illustrates the interaction between a thermocycler device and a computer system. The system comprises a kinetic PCR, analysis module which may be located in a thermocycler device and an intelligence module which is part of the computer system. The data sets (PCR data sets) are transferred from the analysis module to the intelligence module or vice versa via a network connection or a direct connection. The data sets may be processed according to FIG. 12 by computer code running on the processor and being stored on the storage device of the intelligence module and after processing transferred back to the storage device of the analysis module, where the modified data may be displayed on a displaying device.

While the invention has been described by way of example and in terms of the specific embodiments, it is to be understood that the invention is not limited to the disclosed embodiments. To the contrary, it is intended to cover various modifications and similar arrangements as would be apparent to those skilled in the art. Therefore, the scope of the appended claims should be accorded the broadest interpretation so as to encompass all such modifications and similar arrangements.

The invention claimed is:

1. A computer-implemented method of determining a melting temperature, Tm, of DNA, the method comprising the steps, implemented in a computer system having a processor, of:

receiving a dataset representing a melt curve for a DNA sample, the dataset including a plurality of data points each having a pair of coordinate values;
numerically determining first derivative values for data points of the melt curve;
determining a baseline for the first derivative values;
subtracting out the baseline from the first derivative values to produce modified first derivative values;
determining a first maximum value of the modified first derivative values; and
outputting said first maximum value, wherein said first maximum value represents a melting temperature Tm of the DNA sample.

2. The method of claim 1, further comprising the steps of:
calculating an approximation of a curve that fits the modified first derivative values by applying a regression process to a Gaussian Mixture Model function to determine one or more parameters of the function, wherein said parameters include initial conditions, and wherein the first maximum value is used as an initial condition for a first parameter; and
outputting the first parameter, wherein the determined first parameter represents a melting temperature, Tm, of the DNA sample.

3. The method of claim 2, wherein the Gaussian Mixture Model includes an expression of the form:

$$GMM_1 = \mathrm{Exp}(-a_1) \cdot \mathrm{Exp}\left(-\frac{1}{2}\left(\frac{x-\mu_1}{\sigma_1}\right)^2\right),$$

wherein µ1 is the first parameter, and wherein a1 and σ1 are additional parameters.

4. The method of claim 2, further including determining whether the first derivative values includes a shoulder value proximal to the first maximum value.

5. The method of claim 2, further including displaying the first parameter value.

6. The method of claim 2, wherein the regression process includes a Levenberg-Marquardt (LM) regression process.

7. The method of claim 2, further comprising the step of:
determining a second, a third or a fourth maximum value of the modified first derivative values, wherein the second, third or a fourth maximum value is used as an initial condition for a second, third or fourth parameter; and
outputting the second, third or fourth parameter, wherein the determined second, third or fourth parameter represents a second, third or fourth melting temperature, Tm2, Tm3 or Tm4 of the DNA sample.

8. The method of claim 7, wherein the Gaussian Mixture Model includes an expression of the form:

$$GMM_2 = \mathrm{Exp}(-a_1) \cdot \mathrm{Exp}\left(-\frac{1}{2}\left(\frac{x-\mu_1}{\sigma_1}\right)^2\right) + \mathrm{Exp}(-a_2) \cdot \mathrm{Exp}\left(-\frac{1}{2}\left(\frac{x-\mu_2}{\sigma_2}\right)^2\right),$$

wherein µ1 is the first parameter, µ2 is the second parameter and wherein a1, σ1, a2 and σ2 are additional parameters.

9. The method of claim 7, wherein the Gaussian Mixture Model includes an expression of the form:

$$GMM_3 = \mathrm{Exp}(-a_1) \cdot \mathrm{Exp}\left(-\frac{1}{2}\left(\frac{x-\mu_1}{\sigma_1}\right)^2\right) +$$

-continued $$\mathrm{Exp}(-a_2)\cdot\mathrm{Exp}\left(-\frac{1}{2}\left(\frac{x-\mu_2}{\sigma_2}\right)^2\right)+\mathrm{Exp}(-a_3)\cdot\mathrm{Exp}\left(-\frac{1}{2}\left(\frac{x-\mu_3}{\sigma_3}\right)^2\right)$$

wherein $\mu_1$ is the first parameter, $\mu_2$ is the second parameter, $\mu_3$ is the third parameter and wherein a1, σ1, a2, σ2, a3 and σ3 are additional parameters.

10. The method of claim 7, wherein the Gaussian Mixture Model includes an expression of the form:

$$GMM_4 = \mathrm{Exp}(-a_1)\cdot\mathrm{Exp}\left(-\frac{1}{2}\left(\frac{x-\mu_1}{\sigma_1}\right)^2\right)+\mathrm{Exp}(-a_2)\cdot\mathrm{Exp}\left(-\frac{1}{2}\left(\frac{x-\mu_2}{\sigma_2}\right)^2\right)+$$
$$\mathrm{Exp}(-a_3)\cdot\mathrm{Exp}\left(-\frac{1}{2}\left(\frac{x-\mu_3}{\sigma_3}\right)^2\right)+\mathrm{Exp}(-a_4)\cdot\mathrm{Exp}\left(-\frac{1}{2}\left(\frac{x-\mu_4}{\sigma_4}\right)^2\right)$$

wherein $\mu_1$ is the first parameter, $\mu_2$ is the second parameter, $\mu_3$ is the third parameter $\mu_4$ is the fourth parameter and wherein a1, σ1, a2, σ2, a3, σ3, a4 and σ4 are additional parameters.

11. A non-transitory computer readable medium that stores code for controlling a processor to determine a melting temperature, Tm, of DNA, the code including instructions which when executed by the processor causes the processor to perform the steps of claims 1 to 10.

12. A kinetic Polymerase Chain Reaction (PCR) system, comprising: a kinetic PCR analysis device that generates a melt curve dataset representing a DNA melt curve, said dataset including a plurality of data points, each having a pair of coordinate values; and a processor adapted to process the melt curve dataset to determine a Tm value, by performing the steps of claims 1 to 10.

13. The system of claim 12, wherein the kinetic PCR analysis device is resident in a kinetic thermocycler device, and wherein the processor is communicably coupled to the analysis device.

14. The system of claim 12, wherein the processor is resident in a computer system coupled to the analysis device by one of a network connection or a direct connection.

15. The system of claim 12, further including a display module, wherein outputting includes displaying the Tm value on the display module.

16. The system of claim 12, wherein the system is adapted to perform the steps of claims 2 to 10.

17. The system of claim 12, wherein the processor determines a first maximum value by applying a windowing process to the modified first derivative values, wherein the windowing process also determines one or more additional initial conditions for the Gaussian Mixture Model function parameters.

18. The non-transitory computer readable medium of claim 11, wherein the instructions to determine a first maximum value include instructions to apply a windowing process to the modified first derivative values, wherein the windowing process also determines one or more additional initial conditions for the Gaussian Mixture Model function parameters.

19. The method of claim 1, wherein determining a first maximum value includes applying a windowing process to the modified first derivative values, wherein the windowing process also determines one or more additional initial conditions for the Gaussian Mixture Model function parameters.

* * * * *